United States Patent
Duelsner et al.

(10) Patent No.: US 10,755,818 B2
(45) Date of Patent: *Aug. 25, 2020

(54) APPARATUS FOR QUANTIFYING AND DISPLAYING A PATIENT'S TIME BUFFER, BLOOD TREATMENT APPARATUS AND METHOD

(71) Applicants: Fresenius Medical Care Deutschland GmbH, Bad Homburg (DE); Fresenius Medical Care Italia S.p.A, Palazzo Pignano (IT)

(72) Inventors: Erik Duelsner, Florstadt (DE); Marcello Marazzi, Pandino (IL); Wolfgang Wehmeyer, Tübingen (DE)

(73) Assignees: Fresenius Medical Care Deutschland GmbH, Bad Homburg (DE); Fresenius Medical Care Italia S.P.A, Palazzo Pignano (IT)

( * ) Notice: Subject to any disclaimer, the term of this patent is extended or adjusted under 35 U.S.C. 154(b) by 45 days.

This patent is subject to a terminal disclaimer.

(21) Appl. No.: 15/959,434

(22) Filed: Apr. 23, 2018

(65) Prior Publication Data
US 2018/0240555 A1    Aug. 23, 2018

Related U.S. Application Data

(63) Continuation of application No. 14/017,432, filed on Sep. 4, 2013, now Pat. No. 9,977,868.
(Continued)

(30) Foreign Application Priority Data

Sep. 4, 2012  (DE) .................. 10 2012 017 432

(51) Int. Cl.
*G16H 50/30*   (2018.01)
*A61M 1/34*    (2006.01)
(Continued)

(52) U.S. Cl.
CPC .............. *G16H 50/30* (2018.01); *A61M 1/14* (2013.01); *A61M 1/1613* (2014.02); *A61M 1/34* (2013.01);
(Continued)

(58) Field of Classification Search
CPC ................................. G06Q 50/22–24
See application file for complete search history.

(56) References Cited

U.S. PATENT DOCUMENTS 5,656,153 A    8/1997 Kameno et al.
2001/0012917 A1 8/2001 Inukai
(Continued)

FOREIGN PATENT DOCUMENTS

CN    1542671     11/2004
DE   10 2006 032 926   1/2008
(Continued)

OTHER PUBLICATIONS

Nolten, Sven, Prasentation zum Seminarthema, Integrierte Behandlungspfade, Institut fur Medizinische Informatik, RWTH Aachen, Jan. 30, 2010 (obtained Jul. 26, 2016)(with machine translation).
(Continued)

*Primary Examiner* — Robert A Sorey
(74) *Attorney, Agent, or Firm* — Fish & Richardson P.C.

(57) ABSTRACT

An apparatus configured to quantify and display a time buffer for at least one patient during a blood treatment session is described. A blood treatment apparatus which includes such an apparatus or is in signal communication therewith, and a method for quantifying and presenting the time buffer for at least one patient at a blood treatment session are also described, as well as a computer program, a computer program product and a digital storage medium.

15 Claims, 2 Drawing Sheets

Related U.S. Application Data (60) Provisional application No. 61/696,333, filed on Sep. 4, 2012.

(51) Int. Cl.
*A61M 1/14* (2006.01)
*A61M 1/16* (2006.01)
*G06F 19/00* (2018.01)
*G16H 20/40* (2018.01)
*G16H 40/20* (2018.01)

(52) U.S. Cl.
CPC ......... *G06F 19/3481* (2013.01); *G16H 20/40* (2018.01); *A61M 2205/3561* (2013.01); *A61M 2205/50* (2013.01); *A61M 2205/52* (2013.01); *A61M 2205/60* (2013.01); *G16H 40/20* (2018.01)

(56) References Cited

U.S. PATENT DOCUMENTS

| | | |
|---|---|---|
| 2004/0039628 A1 | 2/2004 | Thompson et al. |
| 2004/0267575 A1 | 12/2004 | Boing |
| 2006/0004606 A1 | 1/2006 | Wendl et al. |
| 2009/0281825 A1 | 11/2009 | Larsen |
| 2010/0264086 A1 | 10/2010 | Noack |
| 2010/0298662 A1 | 11/2010 | Yu |
| 2010/0305966 A1 | 12/2010 | Coulter et al. |
| 2011/0069588 A1 | 3/2011 | Tezuka |
| 2012/0029937 A1 | 2/2012 | Neftel et al. |
| 2013/0131574 A1* | 5/2013 | Cosentino ............... A61M 1/28 604/6.07 |
| 2013/0201222 A1 | 8/2013 | Doyle et al. |
| 2013/0274644 A1 | 10/2013 | Hertz |

FOREIGN PATENT DOCUMENTS

| | | |
|---|---|---|
| DE | 10 2009 018 649 | 10/2010 |
| DE | 10 2009 021 255 | 11/2010 |

OTHER PUBLICATIONS

Nolten, Sven, Seminararbeit, Integrierte Behandlungsptade, RWTH Aachen, Instltut fur Medizinische lnformatik, Dec. 15, 2009 (with machine translation).

Wikipedia, Klinischer Behandlungspfad {Clinical Pathway), Jul. 31, 2012, http://de.wikipedia.org. (with English Machine translation).

* cited by examiner

APPARATUS FOR QUANTIFYING AND DISPLAYING A PATIENT'S TIME BUFFER, BLOOD TREATMENT APPARATUS AND METHOD

CROSS REFERENCE TO RELATED APPLICATIONS

The present application is a continuation application of and claims priority to U.S. patent application Ser. No. 14/017,432, filed on Sep. 4, 2013, which claims priority to U.S. Provisional Patent Application Ser. No. 61/696,333, filed on Sep. 4, 2012, and claims priority to Application No. DE 10 2012 017 432.2, filed in the Federal Republic of Germany on Sep. 4, 2012, the entire contents of which are incorporated herein in their entirety by reference thereto.

FIELD OF INVENTION

The present invention relates to an apparatus for quantifying and displaying a patient's time buffer. It further relates to a blood treatment apparatus, a method for quantifying and displaying a time buffer, a computer program, a computer program product and a digital storage medium.

BACKGROUND INFORMATION

Blood treatment centres, such as dialysis centres, are known from practice, where a large number of patients are treated on a daily basis with a limited number of treatment apparatuses, such as dialysis machines. In many of these centres it is thereby necessary to schedule treatments in a multi shift operation. In order to achieve a smooth operation and optimal treatment for each patient, it is important to adhere, as far as possible, to specific times, such as scheduled shift changeover times or the scheduled end time of any queued/upcoming treatment session. Further, adhering to these times can contribute to savings in the costs associated with waiting (shared) taxis.

In order to adhere to these times, it is necessary to know or recognise the individual urgency (which can also be expressed in terms of a "time buffer") with which a specific patient having just arrived at the blood treatment centre should begin the upcoming treatment. It may also be necessary to know how urgently the treatment session of this patient should begin with respect to the urgency for other patients who are, likewise, also waiting to start their treatment sessions and must also be prepared for treatment by medical personnel, (for example by establishing vascular access, measuring body weight, etc.). Not all of the information necessary for recognising the individual urgency is known to medical personnel.

SUMMARY

An object of the present invention is to propose a device and an apparatus for quantifying and displaying a time buffer. Further, a blood treatment apparatus and method are described. In addition, a computer program, a computer program product and a digital storage medium are described.

According to the present invention, an apparatus is proposed which is configured to quantify or identify and display a time buffer or need for urgency in the treatment of at least one patient before and/or during a blood treatment session.

The apparatus according to the present invention includes, at least, a device for reading or importing (herein, reading or importing can also be understood, in some example embodiments according to the present invention, as a readout of) a treatment duration (generally speaking, a treatment duration prescribed and/or intended by the doctor), into the apparatus according into the present invention. The treatment duration states the period of time the patient or his blood should be treated during the blood treatment session in question.

The treatment duration can be read in or imported from, for example, a patient card or from a database with corresponding memory contents. Reading in or importing can also be understood, according to the present invention, as a transfer of a manually input treatment duration between a first and second area or section, by use of the apparatus according the present invention.

A treatment duration can be understood, according to the present invention, as the net treatment duration for a patient, or a pure treatment duration, which does not include the time it takes for setting up and dismantling the treatment apparatus, or treatment apparatus idle periods, during which no blood purification takes place. The treatment duration can, for example, correspond to that given or prescribed by the doctor. The treatment duration can, for example, be every time period (calculated in minutes, for example), in which the treatment apparatus effectively or medically acts on the blood in the manner intended for carrying out the blood purification.

The apparatus according to the present invention further includes at least one device for reading in or importing into the apparatus according to the present invention, at least once, an end time for the blood treatment session—designated or intended by medical personnel, for example.

A blood treatment session end time can be understood according to the present invention as a desired end time for the blood treatment session. The desired end time can be predetermined by medical personnel or the patient, or by external circumstances. The end time can, for example, be dictated by an end of shift in the care of patient(s) in shifts, by an appointment on the part of the patient subsequent to a blood treatment session, by (shared/shuttle) taxis that have been ordered for a particular time, or by any other deadlines or appointments.

The apparatus according to the present invention further includes a device for calculating, identifying or classifying, at least once, a patient's individual time buffer or the need for urgency in an individual patient's treatment. The time buffer or the need for urgency is determined or calculated based on at least, or exclusively, the current time, which correlates to the earliest possible start time for the treatment session, the treatment duration and the end time.

Finally, the apparatus according to the present invention includes a device for outputting or indicating, at least once, a signal which specifies the time buffer or need for urgency or which codes for this.

A time buffer according to the present invention is to be understood as a specification of how much time remains for the patient, or the medical personnel caring for the patient, to begin the treatment (within the meaning of the treatment duration), such that by the (intended and read in) end time, the patient will have been treated over a time span which corresponds with the (intended and read in or imported) treatment duration. If the calculation of the time buffer reveals that a certain amount of time can elapse before the treatment has to begin, and that, nonetheless, by the end time, the treatment duration prescribed for the patient will have still been achieved, this can be described as a positive time buffer. In this case there is no particular need for urgency in starting the treatment.

If, however, the calculation reveals that given the current time, it is no longer possible to offer the patient a treatment that will have lasted the desired treatment duration by the time the end time is reached, then the time buffer can be described as a negative time buffer. The term time buffer as used herein encompasses a time surplus (positive time buffer) as well as a lack of time, or time deficit (negative time buffer). In the event of the latter, there would be an urgent need to begin the patient's treatment, with reference to the total treatment duration (as described above) on the treatment day. Otherwise, the treatment would further overrun the end time, the taxi would have to wait longer, the following appointment or the start of the next patient's treatment—planned to be carried out with the same treatment apparatus—would be delayed, etc. In short, where there is a negative time buffer, the patient is behind schedule.

The assessment of whether a time buffer is positive or negative, and/or whether there is a need for urgency or not, and/or how a classification which may have been carried out is implemented, is also definable as a signal which gives the time buffer, the need for urgency or the corresponding class/category. In this way, a need for urgency can be indicated by, for example, a red warning signal on a monitor, whereas little need for urgency can be indicated with a green signal. The user or producer/manufacturer remains free to specify when a time buffer may still be displayed as green, and when a time buffer should be accompanied by a red indicator.

The terms "time buffer" and "need for urgency" are to be understood herein as synonyms which are used in parallel in order to aid understanding. They are, herein, used interchangeably.

Where a high need for urgency or little need for urgency, or a positive or negative time buffer are discussed herein, then, in certain example embodiments of the present invention, adjectives such as, for example "high," "low," "positive," "negative"—but also all additional adjectives, such as "large," "small" and the like—are correspondingly interpretable as "high," "low," etc., on the basis of a previously predefined criterion. These terms are thus definite as they are measureable against predetermined or established criteria and reflect these.

According to the present invention, a time buffer can also be understood as a treatment status, that is, information concerning which steps of the patients' treatment session have already been executed or carried out (even if the treatment has not yet begun or if, for example, the patient has not yet been connected to the treatment apparatus). These terms, as used herein, can be interchangeable.

A classification can be understood as a pre-defined range/specification of classes/categories, (for example, high, medium, low, or very urgent, little need for urgency, etc.) to which a time buffer can be assigned. The classification does not give the time buffer down to the last quantifiable detail, but instead assigns the time buffer to a class/category from a variety of possible classes/categories, based on the results of the calculations or evaluations.

A coding for the time buffer can be understood as a classification. For example, a positive time buffer may be displayed as a green coloured signal on an indicator, such as a display unit/device. A negative time buffer or a high need for urgency can be displayed as a red coloured signal. Gradations in colour, form and/or appearance are, according to the present invention, also optionally possible if desired. On the other hand, the signal can also be output uncoded. Here, the calculation or evaluation result can be output, for example, as a concrete numerical value (for example in minutes with, for example, a negative sign for a negative time buffer or with a positive sign for a positive time buffer).

The blood treatment apparatus according to the present invention includes at least an/one apparatus according to the present invention, or is connected therewith in unilateral or bilateral signal communication.

The method according to the present invention serves to quantify and display the time buffer or to identify and display the time buffer of at least one patient at, before and/or during a blood treatment session. The method is accomplished with a correspondingly configured apparatus, in particular with an apparatus according to the present invention.

The method according to the present invention encompasses a reading in or importing of the treatment duration with the apparatus.

The method according to the present invention further encompasses reading in or importing, at least once, the end time of the blood treatment session with the apparatus.

Furthermore, the method according to the present invention encompasses at least one calculation, identification or classification of a time buffer with the apparatus. The calculation or identification is based at least, or exclusively, on the current time, the treatment duration and the end time, or integrates these values into the calculation, identification or classification.

Also, the method according to the present invention encompasses at least one output of a signal which gives the time buffer, or which codes therefor, with the apparatus.

A digital, particularly a non-volatile, storage medium according to the present invention, (also termed here as a carrier), particularly in the form of a diskette, RAM, ROM, CD, hard disk, DVD, USB stick, flashcard, SD card or EPROM, particularly with electrically or optically readable control signals, can interact with a computer or computer system such that the mechanical steps of a method according to the invention, as described herein, can be performed.

Thereby all, some, or a few of the mechanically implemented steps of the method according to the invention can be performed.

A computer program product according to the present invention includes a volatile, non-permanent, or a machine readable carrier or program code, saved on a storage medium, for prompting the steps of the method according to the present invention when the computer program product runs on a computer. A computer program product can, according to the present invention, be understood as, for example a computer program saved on a carrier, an embedded system as a comprehensive system with a computer program (e.g., an electronic appliance with a computer program), a network of computer implemented computer programs (e.g. a client-server system, Cloud computing system, etc.), or a computer on which a computer program is loaded, run, saved, implemented or developed.

A machine readable carrier designates in certain example embodiments of the present invention a carrier with contains software and/or hardware interpretable data. The carrier can be a floppy disk, a CD, DVD, a USB stick, a flashcard, an SD card and the like.

A computer program according to the present invention includes a program code for performing the mechanical steps of the method according to the present invention when the computer program runs on a computer. According to the present invention, a computer program can be understood as, for example, a physical software product which is ready for use and includes a program.

It is also true of the computer program product and the computer program according to the present invention, that all, a few or some of the mechanically implemented steps of the method according to the present invention can be implemented.

In all of the above and following descriptions, the use of the expressions, e.g., "can be," "can have," etc., are to be understood as synonyms for "is preferable," "preferably has," etc., and are intended to illustrate an example embodiment according to the present invention.

Example embodiments according to the present invention can include one or several of the features/characteristics described herein.

In certain example embodiments according to the present invention, the time buffer is to be understood as the difference, "end time—treatment duration—current time," or as any other calculation specification/rule which includes the above relationship. If, for example, the treatment session should end at 12:00 (end time) and last 3 hours (treatment duration), then at 9:00 (time) the time buffer will be exactly 0, and at 8:00 the time buffer will amount to one hour. At 8:00 the time buffer can be presented to personnel, dependent on the kind of classification (and coding), as "60 min," or as a green signal. It is self-explanatory that the time buffer constantly changes. For example, the time buffer in the above example can be displayed at 08:30 with a yellow signal and with a red signal at 8:50.

In certain example embodiments according to the present invention, the apparatus includes a device for transmitting, to the blood treatment apparatus, the treatment duration and/or the blood treatment session end time reading.

In some example embodiments according to the present invention, the treatment duration and/or the blood treatment session end time reading are transmitted to the blood treatment apparatus using a network. A network can connect a data carrier/storage medium or a computer with another computer. The blood treatment apparatus can include a computer, a storage device or a computer/calculator/data processor, which are each configured to read in data from a memory using a network.

In some example embodiments according to the present invention, the treatment duration and the blood treatment session end time reading are transmitted to the blood treatment apparatus by a direct reading from the memory of the portable, electronic patient card which is performed by/using a computer in the blood treatment apparatus.

In some example embodiments of the present invention, the steps of the blood treatment session are initiated or activated by directly reading in or importing the treatment duration session and/or by transmitting the blood treatment session end time reading.

In certain example embodiments according to the present invention, the apparatus includes a device which is configured to identify or postpone the required start time of the blood treatment session (the beginning of the blood treatment session can also be termed the start time), or to identify or calculate the time buffer. In this process, the steps required for preparing the blood treatment, or steps required during the blood treatment session during which no treatment of the blood takes place are taken into account and/or the necessary times are taken into account.

Steps that may be required for the execution of the blood treatment can be, for example: connecting the patient to the blood treatment apparatus, measuring the patient's blood pressure before beginning the treatment, automatically or manually executed operating/operational tests to the blood treatment apparatus—which can be executed before or during the blood treatment session—as well as further preparation steps that may be required at the start or end the blood treatment session, such as priming, washing and cleaning disposables. With this device, the start time can be adjusted taking into account the times it takes for the execution of the further/additional steps. This can be done by adding a default value or by adding a flexible time value to the treatment duration, which each include these times as a sum. Hence, the beginning or start time of the blood treatment session is earlier and the treatment session duration is longer than the treatment duration by the value of the default value or the flexible value. Put another way, the time buffer is de facto reduced (or identified as reduced) when the additional necessary steps are taken into account and is thus correspondingly displayed or indicated. The afore-mentioned methods by which the time periods to be taken into account due to the further steps are considered are merely examples for considering the further steps and/or their durations.

In some example embodiments according to the present invention, the apparatus includes a device which is configured to correct the time buffer and/or its display, by the extra time required to execute the further or additional steps. In some example embodiments according to the present invention, such a correction can take place regularly or in response to a cue or query via the blood treatment apparatus or from personnel.

In certain example embodiments according to the present invention, the apparatus includes a device which is configured to read in or import an intended total treatment duration for the patient. The total treatment duration can be understood, according to the present invention, as an added up treatment duration distributed over a predetermined number of treatment sessions. The total treatment duration in these example embodiments according to the present invention is differentiated from the treatment duration as defined above, solely by the fact that it refers to a number x of treatment sessions, whereas the treatment duration refers to each of the queued/upcoming treatment sessions or treatment sessions which have just been implemented. Thus, the total treatment duration is, put simply, also a time duration, prescribed by the doctor, during which the patient's blood is to be actively treated over several treatment sessions. A total treatment duration can, for example refer to a time period of one week. A total treatment duration can, for example, encompass the sum total of the treatment durations from three to five (or more) treatment sessions.

The apparatus further includes a device for adding up the duration that actually took place during which the patient has been medically effectively treated in the frame of the pre-determined number—for example, a number x-1—of subsequently carried out treatment sessions.

The apparatus further includes a device for determining or revising the treatment duration reading for the queued/upcoming treatment session, taking into account the treatment duration reading and the sum total of the duration of the treatments that have already taken place. The apparatus can determine the duration of the blood treatment session on the basis of blood treatment sessions that have already executed. If, for example, in at least one of the treatment sessions, the patient was treated for longer than the total treatment time divided by the pre-determined number of treatment sessions (each treatment session is assumed here to have the same duration), then the duration of the current treatment session can possibly be shortened, when compared to the duration prescribed for this treatment session. In certain circumstances, this may be found to be beneficial, with respect to patient time-management and the treatment centre's organizational procedures. Equally, the duration of the current treatment of the current treatment session can also be extended. This would provide the patient with a treatment "buffer," the length of which would be deducted at a later treatment session, meaning s/he would be connected to the treatment machine in this later treatment session for less than the prescribed treatment duration.

"Taking into account the total treatment session reading" can, according to the present invention, be understood as establishing a difference, or a calculation rule in which this difference, or a part thereof, is worked out mathematically. In this way, a total treatment duration can be determined, which enables the patient to be treated over three consecutive treatment sessions for a total of 12 hours (total treatment session). However, if the patient has already been treated over 8.5 hours (summed up durations), for example, the read in treatment duration of 4 hours may be set or amended for the subsequent treatment session as 12 h–8.5 h=3.5 h.

In some example embodiments according to the present invention, a treatment duration adjusted in this way can be used instead of the treatment duration reading to identify the time buffer. The apparatus according to the present invention is, in these example embodiments correspondingly configured or includes such a device. In some example embodiments according to the present invention, in which an adjustment of this sort is made, which adjustment is limited by restrictions, a negative time buffer may possibly turn into a positive one.

In certain example embodiments according to the present invention, the apparatus includes a device which is configured for entering a shortened treatment duration in comparison to the read in or imported treatment duration reading, (on the basis of, for example, a negative time buffer, or the identification of such a time buffer or a higher need for urgency), but which is also configured for entering an extended treatment duration via the apparatus. The read in or imported treatment duration can, in some cases, be too long to be obliged with, because of the advanced time of the treatment session and the need to adhere to the determined end time. In this case, the patient is ascribed a negative time buffer. In order to adhere to the end time, which is necessary in certain cases, the device is configured such that the treatment duration (when compared to the read in treatment duration) must be newly entered or newly read, and in this process it is shortened or may be shortened or taken as shortened in order that the determined end time can be adhered to. Likewise, provision can be also made for extending the treatment duration in order to use the time until the end time beyond the read in treatment duration for the treatment.

The apparatus according to the present invention can include a device or entity which ensures that the new, shortened treatment duration does not fall below a predetermined minimum treatment duration, even if the blood treatment session cannot—and this is/would be recognizable at an early stage—be ended by the end time.

In certain example embodiments according to the present invention, the apparatus includes a device for multiple queries or the identification of the progress of the treatment of the patient, in short, an interrogator. The query takes place with a correspondingly configured interrogator, during the treatment session, via a readout or via the identification of initiated or completed interruptions by the treatment apparatus to the patient's treatment. Such interruptions are to be understood as suspensions in the treatment. During such interruptions, the patient is not medically treated with the treatment apparatus. During such interruptions, the remainder of the treatment duration is not reduced.

In these example embodiments according to the present invention, the apparatus further includes a device for identifying or appraising, by use of the interrogator, the total duration of the identified interruptions to the treatment (or some or all of the identified interruptions which are of a particular type, belong to a particular class, include a minimum duration, or the like).

Further, the apparatus in these example embodiments according to the present invention includes a device which is configured to calculate, identify or classify the time buffer or the need for urgency. In this process at least the actual time, the treatment duration, the total duration of the identified or accumulated interruptions, and the end time are taken into account, or they are included in the calculation, identification or classification. The "device" can refer to one of the devices already described above.

In some example embodiments according to the present invention, the apparatus includes a device which is configured to compare time buffers or the need for urgency between multiple patients and to determine a treatment sequence/order for these patients on the basis of this comparison.

The result of the comparison can in turn be indicated or output with one or more suitable signals. This can, for example, be in the form of a sequential order in which the personnel attend individual patients. The result of the comparison can, alternatively, take the form of pooling patients in various categories of priority, or in other ways.

In some example embodiments according to the present invention, the apparatus includes a device which is configured to newly determine the end time and/or the treatment duration on the basis of a time buffer which falls under a predetermined threshold, or if such time buffer is detected.

Each of the devices of the apparatus according to the present invention described herein can be specially configured, or prepared in some other way, to perform each of the method steps, even if this is not explicitly described herein.

Each of the devices of the apparatus according to the present invention described herein can be expressly configured, or prepared in some other way, to perform more than one of the method steps described herein.

Combinations of features according to the methods according to the present invention are also possible, which are not fully described here, solely to avoid repetition.

The statements and definitions relating to the apparatus according to the present invention are also relevant to the methods according to the present invention, where this gives rise to no contradiction for persons skilled in the art.

Some or all of the example embodiments according to the present invention can include one, several or all of the advantages described above and/or below.

The quantification and display of time buffers according to the present invention can achieve the following advantages with respect to patient management: reduced waiting time for patients waiting for transport to and from the blood treatment site (so called "taxi waiting times"), improved and predictable workflow for attendant medical personnel, lower stress levels for personnel and patients and thus lower hygiene risks during the blood treatment, departure of patients from the blood treatment room within a given time slot allowing the blood treatment room to be cleaned according to hygiene and efficiency regulations.

The apparatus according to the present invention and the method according to the present invention can advantageously improve the quality of life for patients insofar as they need spend only the required amount of time in the blood treatment room and at the blood treatment centre. Furthermore, this leads to reduced costs for the blood treatment centre.

Example embodiments of the present invention are exemplarily described with reference to the accompanying drawings, in which the same reference numerals denote the same or similar components. Some aspects of the figures are highly simplified.

DETAILED DESCRIPTION

Figure 1:
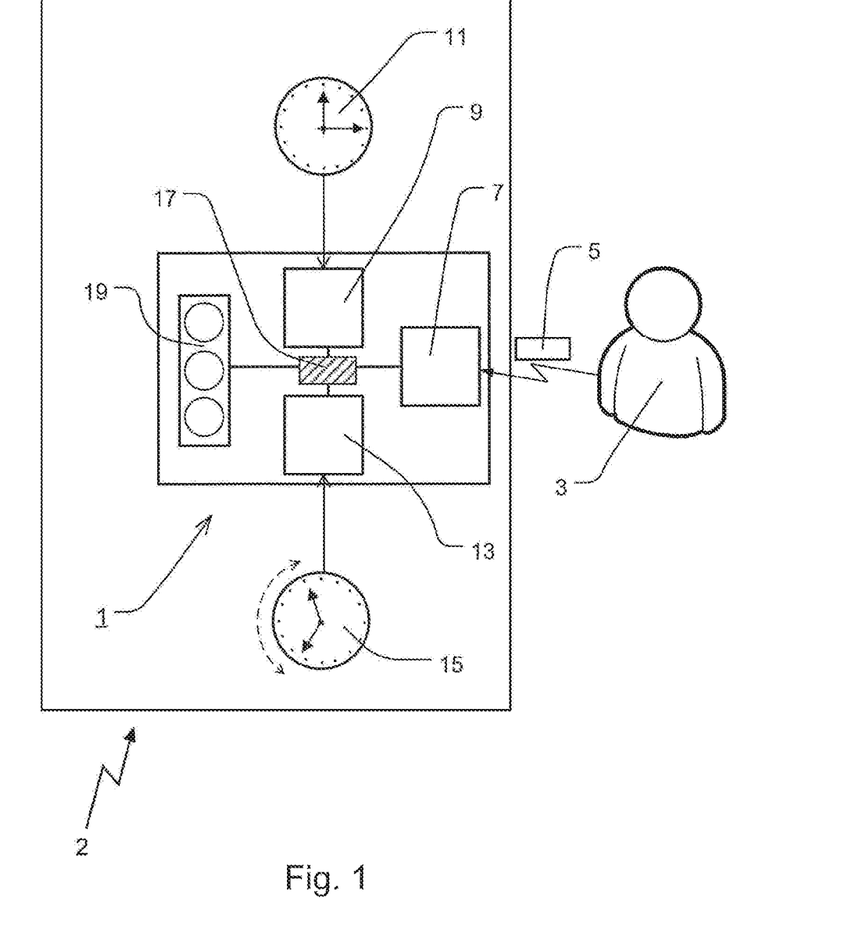
FIG. 1 shows a schematically simplified apparatus according to the present invention, embedded in a blood treatment apparatus, for quantifying and displaying a time buffer.

FIG. 1 shows a schematically simplified apparatus 1 according to the present invention, which is part of a blood treatment apparatus 2 according to the present invention and which quantifies and displays a patient's 3 time buffer during a blood treatment session.

A treatment duration 15 for the patient's 3 blood treatment session is, in this exemplary embodiment, saved on a patient card 5, which the patient can bring to the blood treatment session, for example. The treatment duration 15 is saved beforehand on the patient card 5 at the treating nephrologist's clinic, for example. The treatment duration 15 is read from the patient card 5 by means of a device 7 which is a reader for the patient card. The device 7 is part of apparatus 1.

The apparatus 1 further comprises a device 9 for reading the end time 11 of a blood treatment session. This reading can be carried out by a data network and another data reading device located elsewhere. According to the present invention, the data entry can also be read using a keyboard or touchscreen.

Apparatus 1 further comprises a device 13 for reading the treatment duration 15 of the blood treatment session. The reading is carried out by the same or similar principles as those for reading the end time 11.

In this exemplary embodiment, the input data is processed by means of a processor 17. The calculation by the processor 17 results in either a positive or negative time buffer. This time buffer is output or displayed by means of a device 19 of apparatus 1.

Alternatively, (not shown here), the device 19 can be located outside of the apparatus 1, or the results of the calculation can be transmitted to a further device located outside the apparatus 1, for example a PDA (personal digital assistant), a Blackberry, a mobile cordless communication or organization assistant, or the like.

For persons skilled in the art, it is evident that apparatus 1 according to the present invention does not have to be fixed to, or near, a blood treatment apparatus 2 according to the present invention, and nor does it have to be a part thereof. The present invention is not limited in this way. It is sufficient for the apparatus 1 and the blood treatment apparatus 2 to have a signal connection (unidirectional or bidirectional) with each other.

Figure 2:
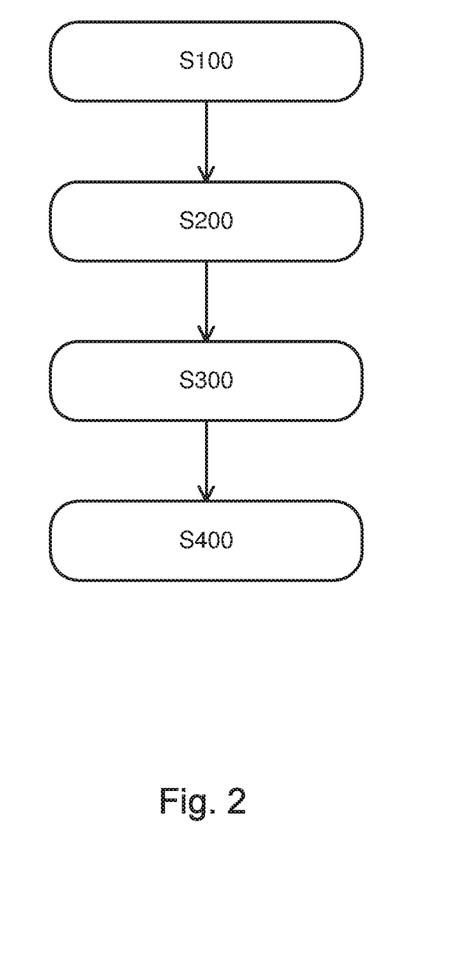
FIG. 2 schematically shows in a flow diagram the steps of the method according to the present invention for quantifying and displaying a time buffer, in one example embodiment.

FIG. 2 shows exemplarily in a flow diagram the steps of the method according to the present invention for quantifying and displaying a time buffer in one exemplary embodiment.

In a first step S100, the treatment duration is read in or imported to the apparatus 1 according to the present invention from the patient card 5. This is carried out by, for example, a device 7 for reading the treatment duration such as a card reader.

In a following step S200, the end time 11 of the blood treatment session is read via apparatus 1, for example, by a device 9 for reading the end time. Alternatively, the end time can be read by a data network from another computer, a storage device etc.

The chronological order of the steps S100 and S200 in this process are discretionary.

In a further step S300, a positive or negative time buffer is calculated via the apparatus 1. The calculation is carried out by, for example, a processor 17 in the apparatus 1. The current time, the time duration reading from step S100, and blood treatment session end time reading from step S200 are included or considered in the calculation.

When, for example, the calculation shows that the current time as a potential start time for the blood treatment session, together with blood treatment duration reading, result in the end time reading being precisely met, then the time buffer is neither positive nor negative. Nevertheless, the apparatus 1 can indicate that the patient's blood treatment session should begin urgently.

If the calculations between the current time as potential start time for the blood treatment session and the treatment duration reading determine that there will still be time left before the end time, then the time buffer is positive. A positive time buffer can, for example, be used to commence the blood treatment session of another patient for whom a negative time buffer has been calculated. Alternatively, the treatment duration can, at short notice, be extended by the length of the positive time buffer and the treatment session can begin ahead of schedule. The patient's time buffer is adjusted based on the amended treatment duration.

A negative time buffer is determined or found when, for example, the end time reading will be exceeded, even if the treatment duration reading is complied with and the blood treatment session starts promptly. A negative time buffer can, for example, make it possible to shorten/contract the treatment duration.

In a further step S400, the time buffer is indicated. In FIG. 1 the time buffer is indicated by a device 19 for outputting or displaying the time buffer. The device in this exemplary embodiment is arranged as a kind of traffic light. The upper circle can show a red signal to indicate a negative time buffer. The lower circle can show a green signal to indicate a positive time buffer. The middle circle can show a yellow signal to indicate that the time buffer is neither positive nor negative.

LIST OF REFERENCE NUMERALS

| Reference Numeral | Description |
| --- | --- |
| S100 | Step for reading in or importing the treatment duration |
| S200 | Step for reading in or importing the end time |
| S300 | Calculation of the time buffer |
| S400 | Time buffer display |
| 1 | Apparatus |
| 2 | Blood treatment apparatus |

-continued

| Reference Numeral | Description |
| --- | --- |
| 3 | Patient |
| 5 | Patient card |
| 7 | Device for reading in or importing the treatment duration |
| 9 | Device for reading in or importing the end time |
| 11 | Treatment session end time |
| 13 | Device for reading or importing the treatment duration |
| 15 | Treatment duration of the blood treatment session |
| 17 | Device for calculating the time buffer |
| 19 | Device for outputting or displaying the time buffer |

What is claimed is:

1. A blood treatment machine and an apparatus that is part of or connected in signal communication to the blood treatment machine, the apparatus comprising:
a first device configured to read in or import a prescribed treatment duration for a patient;
a second device configured to read in or import a target end time for a blood treatment session for the patient;
a third device configured to calculate a time buffer wherein the time buffer is calculated by subtracting a current time and the prescribed treatment duration from the target end time, wherein the calculated time buffer is a first amount of time;
a fourth device configured to output or display: (i) a signal that is coded in correspondence to the calculated time buffer or (ii) the first amount of time;
a fifth device configured to, in response to the first amount of time being negative, read in or import a prescribed total treatment duration for the patient, the prescribed total treatment duration being a sum total of prescribed treatment durations of a plurality of consecutive treatment sessions;
the third device configured to add up a total of actual treatment durations of the plurality of consecutive blood treatment sessions that were previously executed to treat the patient;
the third device configured to calculate a treatment buffer by subtracting the prescribed total treatment duration from the total of actual treatment durations, wherein the calculated treatment buffer is a second amount of time;
the third device configured to, in response to the second amount of time being positive, calculate an adjusted treatment duration for the patient, wherein the adjusted treatment duration is calculated by subtracting the calculated treatment buffer from the prescribed treatment duration; and
the third device configured to calculate an adjusted time buffer, wherein the adjusted time buffer is calculated by subtracting the adjusted treatment duration and the current time from the target end time, wherein the adjusted time buffer is a third amount of time,
the blood treatment machine configured to, in response to the third amount of time being positive, (i) receive the adjusted treatment duration and (ii) be started to treat the patient.

2. The blood treatment machine and the apparatus according to claim 1, wherein the third device is configured to calculate the adjusted time buffer by also subtracting a total time needed to carry out further required steps of the blood treatment session during which no treatment of the patient's blood will take place.

3. The blood treatment machine and the apparatus according to claim 1, further comprising:
a device adapted to input a shortened or extended treatment duration in place of the read in or imported prescribed treatment duration, and wherein the third device is configured to calculate the time buffer on a basis of at least the current time, the shortened or extended treatment duration, and the target end time.

4. The blood treatment machine and the apparatus according to claim 1, further comprising:
a device adapted for multiple queries or multiple identifications of a progress of the patient's blood treatment session by use of an interrogator which identifies interruptions during the blood treatment session via reading out or identifying interruptions completed or initiated by the blood treatment machine or the apparatus;
a device adapted for determining a total length of time of the interruptions to the blood treatment session identified by the interrogator; and
wherein the third device is configured to calculate the time buffer by also subtracting the total length of time of the interruptions from the target end time.

5. A blood treatment method that is carried out by a blood treatment machine and an apparatus which is part of or connected in signal communication to the blood treatment machine, the method comprising:
reading in or importing, using a first device of the apparatus, a prescribed treatment duration for a patient;
reading in or importing, using a second device of the apparatus, a desired end time for a blood treatment session for the patient;
calculating, using a third device of the apparatus, a time buffer, wherein the time buffer is calculated by subtracting a current time and the prescribed treatment duration from the desired end time, wherein the calculated time buffer is a first amount of time;
outputting or displaying using a fourth device of the apparatus: (i) a signal that is coded in correspondence to the calculated time buffer or (ii) the first amount of time;
in response to the first amount of time being negative, reading in or importing, using a fifth device of the apparatus, a prescribed total treatment duration for the patient, the prescribed total treatment duration being a sum total of prescribed treatment durations of a plurality of consecutive blood treatment sessions;
adding up, using the third device, a total of actual treatment durations of the plurality of consecutive blood treatment sessions that were previously executed to treat the patient;
calculating, using the third device, a treatment buffer by subtracting the prescribed total treatment duration from the total of actual treatment durations, wherein the calculated treatment buffer is a second amount of time;
in response to the second amount of time being positive, calculating, using the third device, an adjusted treatment duration for the patient, wherein the adjusted treatment duration is calculated by subtracting the calculated treatment buffer from the prescribed treatment duration; and
calculating, using the third device, an adjusted time buffer, wherein the adjusted time buffer is calculated by subtracting the adjusted treatment duration and the current time from the desired end time, wherein the adjusted time buffer is a third amount of time, the blood treatment machine configured to, in response to the third amount of time being positive, (i) receive the adjusted treatment duration and (ii) be started to treat the patient.

6. The method according to claim 5, further comprising determining, using the third device, an amount of time necessary to execute further required steps for execution of the blood treatment session, and calculating the time buffer, using the third device, by subtracting the amount of time necessary to execute the further required steps from the desired end time.

7. The method according to claim 5, further comprising:
newly specifying or setting anew the end time and/or the treatment duration via the apparatus on a basis of a time buffer which falls under a predetermined threshold or if such a time buffer is detected.

8. The method according to claim 5, further comprising:
comparing, using the third device, the calculated adjusted treatment duration to a predetermined minimum treatment duration, and
wherein the blood treatment machine is configurable to be started to treat the patient contingent on the calculated adjusted treatment duration being equal to or greater than the predetermined minimum treatment duration.

9. The method according to claim 5, further comprising:
performing multiple queries or multiple identifications of a progress of the patient's blood treatment session by use of an interrogator of the apparatus during the patient's blood treatment session, the interrogator identifying interruptions during the patient's blood treatment session by reading out or identifying interruptions completed or initiated by the blood treatment machine or the apparatus; and
determining, by the third device, a total length of time of the identified interruptions to the blood treatment session identified by the interrogator, and
wherein the calculating the time buffer also includes subtracting the total length of time of the identified interruptions from the desired end time.

10. A non-transitory computer-readable digital storage medium with an executable program stored thereon, wherein the program instructs a programmable computer system to perform a blood treatment method that is carried out by a blood treatment machine and an apparatus which is part of or connected in signal communication to the blood treatment machine, the method comprising:
reading in or importing, using a first device of the apparatus, a prescribed treatment duration for a patient;
reading in or importing, using a second device of the apparatus, a desired end time for a blood treatment session for the patient;
calculating, using a third device of the apparatus, a time buffer, wherein the time buffer is calculated by subtracting a current time and the prescribed treatment duration from the desired end time, wherein the calculated time buffer is a first amount of time;
outputting or displaying using a fourth device of the apparatus: (i) a signal that is coded in correspondence to the calculated time buffer or (ii) the first amount of time;
in response to the first amount of time being negative, reading in or importing, using a fifth device of the apparatus, a prescribed total treatment duration for the patient, the prescribed total treatment duration being a sum total of prescribed treatment durations of a plurality of consecutive blood treatment sessions;
adding up, using the third device, a total of actual treatment durations of the plurality of consecutive blood treatment sessions that were previously executed to treat the patient;
calculating, using the third device, a treatment buffer by subtracting the prescribed total treatment duration from the total of actual treatment durations, wherein the calculated treatment buffer is a second amount of time;
in response to the second amount of time being positive, calculating, using the third device, an adjusted treatment duration for the patient, wherein the adjusted treatment duration is calculated by subtracting the calculated treatment buffer from the prescribed treatment duration; and
calculating, using the third device, an adjusted time buffer, wherein the adjusted time buffer is calculated by subtracting the adjusted treatment duration and the current time from the desired end time, wherein the adjusted time buffer is a third amount of time,
the blood treatment machine configured to, in response to the third amount of time being positive, (i) receive the adjusted treatment duration and (ii) be started to treat the patient.

11. The method according to claim 5, further comprising:
conducting the blood treatment session to treat the patient for a period of time corresponding to the adjusted treatment duration.

12. The blood treatment machine and the apparatus according to claim 1, wherein the fourth device is configured to output or display the first amount of time as a numerical value.

13. The blood treatment machine and the apparatus according to claim 1, wherein the signal is a colored indicator displayed on a display unit.

14. The method according to claim 5, wherein the fourth device outputs or displays the first amount of time as a numerical value.

15. The method according to claim 5, wherein the signal is a colored indicator displayed on a display unit.

* * * * *